US010369073B2

(12) United States Patent
Rosario et al.

(10) Patent No.: US 10,369,073 B2
(45) Date of Patent: Aug. 6, 2019

(54) SKIN TREATMENT APPARATUS AND PARTS THEREOF

(71) Applicants: Luis del Rosario, Glendale, CA (US); Lee del Rosario, Glendale, CA (US)

(72) Inventors: Luis del Rosario, Glendale, CA (US); Lee del Rosario, Glendale, CA (US)

( * ) Notice: Subject to any disclaimer, the term of this patent is extended or adjusted under 35 U.S.C. 154(b) by 665 days.

(21) Appl. No.: 14/828,777

(22) Filed: Aug. 18, 2015

(65) Prior Publication Data

US 2016/0051436 A1 Feb. 25, 2016

Related U.S. Application Data

(60) Provisional application No. 62/040,912, filed on Aug. 22, 2014.

(51) Int. Cl.
*A61H 7/00* (2006.01)
*A61N 5/06* (2006.01)

(52) U.S. Cl.
CPC .......... *A61H 7/008* (2013.01); *A61N 5/0616* (2013.01); *A61N 5/0624* (2013.01); *A61H 2201/0153* (2013.01); *A61H 2201/0188* (2013.01); *A61H 2201/10* (2013.01); *A61H 2201/105* (2013.01); *A61H 2201/1685* (2013.01); *A61H 2201/1692* (2013.01); *A61N 2005/063* (2013.01); *A61N 2005/0649* (2013.01)

(58) Field of Classification Search
CPC ............ A61H 7/008; A61H 2201/1692; A61H 2201/1685; A61H 2201/10; A61H 2201/105; A61H 2201/0153; A61H 2201/0188; A61N 5/0624; A61N 5/0616; A61N 2005/0649; A61N 2005/063
See application file for complete search history.

(56) References Cited

U.S. PATENT DOCUMENTS

| | | | |
|---|---|---|---|
| 6,299,620 B1 | 10/2001 | Shadduck | |
| 6,641,591 B1 | 11/2003 | Shadduck | |
| 7,678,120 B2 | 3/2010 | Shadduck | |
| 7,789,886 B2 | 9/2010 | Shadduck | |
| 8,066,716 B2 | 11/2011 | Shadduck | |
| 8,337,513 B2 | 12/2012 | Shadduck | |
| 2008/0262394 A1* | 10/2008 | Pryor | A61H 7/007 601/15 |
| 2010/0312157 A1* | 12/2010 | Yan | A61H 7/005 601/112 |

* cited by examiner

*Primary Examiner* — Sundhara M Ganesan
(74) *Attorney, Agent, or Firm* — Kevin Schraven; Anooj Patel; Hankin Patent Law, APC

(57) ABSTRACT

A skin treatment apparatus. The skin treatment apparatus may comprise: an applicator tool, a vacuum source, fluid reservoir, and first tube. The applicator tool may comprise: a tip, a head, and a body. The head is removeably connected to a distal end of the body. The tip is preferably positioned substantially within the head and may comprise one or more contact members. The contact members may comprise a contact surface. The contact surface are generally nonabrasive and are configured to contact a skin surface. The vacuum source may provide a vacuum to the applicator tool to create a suction. The tip may comprise at least one opening that is in fluid communication with the fluid reservoir via the first tube. The fluid reservoir may store a fluid, which may pass through the first tube, through the opening of the tip, and drawn outside the tip via the vacuum.

16 Claims, 13 Drawing Sheets

SKIN TREATMENT APPARATUS AND PARTS THEREOF

CROSS-REFERENCE TO RELATED APPLICATIONS

This application claims the benefit of U.S. Provisional Patent Application No. 62/040,912, filed on Aug. 22, 2014, titled "Skin Treatment Apparatus", by co-inventors Luis del Rosario and Lee del Rosario, the contents of which are expressly incorporated herein by this reference and set forth in its entirety.

FIELD OF USE

The present disclosure relates generally to dermatological devices, and more specifically, to dermatological applicator tools with non-abrasive tips for exfoliating and skin rejuvenating procedures.

BACKGROUND

For years, dermatologists have developed and performed various types of skin treatments and methods to enhance, rejuvenate, and/or improve the surface of the skin of individuals. Such methods may generally include skin resurfacing techniques such as dermabrasion and microdermabrasion, which are typically designed to remove the upper and outermost layers of a person's skin. Dermabrasion is a skin-resurfacing procedure that utilizes a rapid rotating device to sand or exfoliate the outer layers of skin. Microdermabrasion, on the other hand, utilizes rough, tiny grains to buff away the outer layer of a person's skin. These techniques usually induce new skin growth at the treated area for smoother and healthier looking skin, and both procedures can decrease the overall appearance of wrinkles and facial lines. These techniques can also improve the look of scars, such as those caused by acne.

Devices used for dermabrasion and microdermabrasion procedures generally utilize abrasive tips and/or rotating brushes coated with abrasive particles. These abrasive tips have been used to remove the outer skin layers and are sometimes used aggressively. As a result, when performing these procedures, a person's skin may encounter some problems or be damaged. For example, dermabrasion and microdermabrasion may alter the skin's color balance by creating light or dark patches on the person's skin. Additionally, scarring and pigmentary changes may result due to the abrasive surfaces of the devices. Although these potential risks are small, individuals with darker skin tones are more prone to potential altered pigmentation problems.

Therefore, what is needed is dermatological device that keeps the benefits, but minimizes the risks associated with dermabrasion and microdermabrasion treatments. Preferably, the new and improved skin rejuvenating device will utilize a non-abrasive tip to promote collagen and skin growth while preventing scarring and discoloration.

SUMMARY

To minimize the limitations in the prior art, and to minimize other limitations that will become apparent upon reading and understanding the present specification, the following discloses a new and improved skin treatment apparatus.

One embodiment may be a skin treatment apparatus, comprising: an applicator tool; and a vacuum source; wherein the applicator tool comprises: a tip, a head, and a body; wherein the head is removeably connected to a distal end of the body; wherein the tip is positioned substantially within the head; wherein the tip comprises one or more contact members; wherein the one or more contact members comprise one or more contact surfaces; wherein the one or more contact surfaces of the tip may be nonabrasive and may be configured to contact a skin surface; wherein the vacuum source provides a vacuum throughout the applicator tool, such that the vacuum is drawn from the distal end of the head and around the tip to a proximal end of the body of the applicator tool to create a suction; and wherein the suction is configured to draw a portion of the skin surface into contact with the one or more contact surfaces of the tip. The one or more contacting surfaces of the tip may be substantially flat and cylindrical. The one or more contact surfaces of the tip may be substantially hemispherical. The one or more contact surfaces of the tip may be generally smooth and lack any purposefully abrasive elements. The skin treatment apparatus may further comprise a fluid reservoir and a first tube; wherein the tip may comprise at least one opening that is in fluid communication with the fluid reservoir via the first tube; wherein the fluid reservoir may be configured to store a fluid and to provide the fluid through the at least one opening of the tip of the applicator tool, such that the liquid may contact the skin surface when the head contacts the skin surface; and wherein the fluid may be configured to pass through the first tube, through the at least one opening of the tip, and drawn outside the tip and within the applicator tool via the vacuum. The skin treatment apparatus may further comprise a second tube, an optical fiber, and a light source; wherein the second tube may be configured to connect to the light source; wherein the optical fiber may be positioned within the first tube of the applicator tool and may extend from the applicator tool, through the second tube, and to the light source; and wherein the optical fiber is configured to emit a light. The light may be configured to sterilize the fluid. The light may be configured to sterilize the skin surface. The at least a portion of the applicator tool may be transparent, such that the light may be visible to a user when the applicator tool is in use. The skin treatment apparatus may further comprise a ball member and a vacuum tube; wherein the vacuum tube may be connected to the vacuum source; and wherein the ball member may interconnect the applicator tool, the first tube, the second tube, and the vacuum tube.

Another embodiment may be a skin treatment apparatus, comprising: an applicator tool; a vacuum source; a fluid reservoir; and a first tube; wherein the applicator tool comprises: a tip, a head, and a body; wherein the head is removeably connected to a distal end of the body; wherein the tip is positioned substantially within the head and comprises one or more contact members; wherein the one or more contact members comprise one or more contact surfaces; wherein the one or more contact surfaces of the tip may be nonabrasive and may be configured to contact a skin surface; wherein the vacuum source provides a vacuum throughout the applicator tool, such that the vacuum is drawn from a distal end of the head and around the tip to a proximal end of the body of the applicator tool to create a suction; wherein the suction is configured to draw a portion of the skin surface into contact with the contact surface of the tip; wherein the tip comprises at least one opening that is in fluid communication with the fluid reservoir via the first tube; wherein the fluid reservoir is configured to store a fluid and to provide the fluid through the at least one opening of the tip of the applicator tool, such that the liquid contacts the skin surface when the head contacts the skin surface; and wherein the fluid is configured to pass through the first tube, through the at least one opening of the tip, and drawn outside the tip and within the applicator tool via the vacuum. The one or more contacting surfaces of the tip may be substantially flat and cylindrical. The one or more contact surfaces of the tip may be substantially hemispherical. The one or more contact surfaces of the tip may be generally smooth and lack any purposefully abrasive elements. The skin treatment apparatus may further comprise a second tube, an optical fiber, and a light source; wherein the second tube may be configured to connect to the light source; wherein the optical fiber may be located within the first tube of the applicator tool and may extend from the applicator tool, through the second tube, and to the light source; and wherein the optical fiber may be configured to emit a light. The light may be configured to sterilize the fluid. The light may be configured to sterilize the skin surface. At least a portion of the applicator tool may be transparent, such that the light may be visible to a user when the applicator tool is in use. The skin treatment apparatus may further comprise a ball member and a vacuum tube; wherein the vacuum tube may be connected to the vacuum source; and wherein the ball member may interconnect the applicator tool, the first tube, the second tube, and the vacuum tube. The head of the applicator tool may be configured to rotate via a motor.

Another embodiment may be a skin treatment apparatus, comprising: an applicator tool; a vacuum source; a fluid reservoir; a first tube; a second tube; an optical fiber; a light source; a ball member; and a vacuum tube; wherein the applicator tool comprises: a tip, a head, and a body; wherein the head is removeably connected to a distal end of the body; wherein the tip is positioned substantially within the head and comprises one or more contact members; wherein the one or more contact members comprise one or more contact surfaces; wherein the one or more contact surfaces of the tip may be nonabrasive and may be configured to contact a skin surface; wherein the one or more contacting surfaces of the tip is substantially flat and cylindrical; the one or more contact surfaces of the tip may be generally smooth and lack any purposefully abrasive elements; wherein the vacuum source provides a vacuum throughout the applicator tool, such that the vacuum is drawn from a distal end of the head and around the tip to a proximal end of the body of the applicator tool to create a suction; wherein the suction is configured to draw a portion of the skin surface into contact with the contact surface of the tip; wherein the tip comprises at least one opening that is in fluid communication with the fluid reservoir via the first tube; wherein the fluid reservoir is configured to store a fluid and to provide the fluid through the at least one opening of the tip of the applicator tool, such that the liquid contacts the skin surface when the head contacts the skin surface; wherein the fluid is configured to pass through the first tube, through the at least one opening of the tip, and drawn outside the tip and within the applicator tool via the vacuum; wherein the second tube is configured to connect to the light source; wherein the optical fiber is located within the first tube of the applicator tool and extends from the applicator tool, through the second tube, and to the light source; wherein the optical fiber is configured to emit a light; wherein the light is configured to sterilize the fluid and the skin surface; wherein at least a portion of the applicator tool is transparent, such that the light is visible to a user when the applicator tool is in use; wherein the vacuum tube is connected to the vacuum source; and wherein the ball member interconnects the applicator tool, the first tube, the second tube, and the vacuum tube.

Another embodiment may a skin treatment apparatus, comprising: an applicator tool; and a vacuum source; wherein the applicator tool comprises: a tip, a head, and a body; wherein the head is removeably connected to a distal end of the body; wherein the tip is positioned substantially within the head; wherein a contact surface of the tip and the head may be nonabrasive and may be configured to contact a skin surface; wherein the vacuum source provides a vacuum throughout the applicator tool, such that the vacuum is drawn from a distal end of the head and around the tip to a proximal end of the body of the applicator tool to create a suction; and wherein the suction is configured to draw a portion of the skin surface into contact with the contact surface of the tip. The contacting surface of the tip may comprise one or more support members, such that the contacting surface of the tip is substantially non-planar. At least a portion of each of the one or more contact members may be one or more contact surfaces that may be substantially circular. The one or more contact surfaces may be one or more spherically shaped balls held onto the tip by a cage. The skin treatment apparatus may further comprise a fluid reservoir and a first tube; wherein the tip may comprise at least one opening that is in fluid communication with the fluid reservoir via the first tube; wherein the fluid reservoir may be configured to store a fluid and to provide the fluid through the at least one opening of the tip of the applicator tool, such that the liquid may contact the skin surface when the head contacts the skin surface; and wherein the fluid may be configured to pass through the first tube, through the at least one opening of the tip, and drawn outside the tip and within the applicator tool via the vacuum. The skin treatment apparatus may further comprise a second tube, an optical fiber, and a light source; wherein the second tube may be configured to connect to the light source; wherein the optical fiber may be located within the first tube of the applicator tool and extends from the applicator tool, through the second tube, and to the light source; and wherein the optical fiber may be configured to emit a light. The light may be configured to sterilize the fluid. The light may be configured to sterilize the skin surface. At least a portion of the applicator tool may be transparent, such that the light is visible to a user when the applicator tool is in use. The skin treatment apparatus may further comprise a ball member and a vacuum tube; wherein the vacuum tube may be connected to the vacuum source; and wherein the ball member may interconnect the applicator tool, the first tube, the second tube, and the vacuum tube.

Another embodiment may be a skin treatment apparatus, comprising: an applicator tool; a vacuum source; a fluid reservoir; and a first tube; wherein the applicator tool comprises: a tip, a head, and a body; wherein the head is removeably connected to a distal end of the body; wherein the tip is positioned substantially within the head and comprises one or more support members, such that a contacting surface of the tip is substantially non-planar; wherein the contact surface of the tip and the head may be nonabrasive and may be configured to contact a skin surface; wherein the vacuum source provides a vacuum throughout the applicator tool, such that the vacuum is drawn from a distal end of the head and around the tip to a proximal end of the body of the applicator tool to create a suction; wherein the suction is configured to draw a portion of the skin surface into contact with the contact surface of the tip; wherein the tip comprises at least one opening that is in fluid communication with the fluid reservoir via the first tube; wherein the fluid reservoir is configured to store a fluid and to provide the fluid through the at least one opening of the tip of the applicator tool, such that the liquid contacts the skin surface when the head contacts the skin surface; and wherein the fluid is configured to pass through the first tube, through the at least one opening of the tip, and drawn outside the tip and within the applicator tool via the vacuum. At least a portion of each of the one or more contact members may be one or more contact surfaces that may be substantially circular and may be fixed on the tip. The one or more contact surfaces may be one or more spherically shaped balls held onto the tip by a cage. The skin treatment apparatus may further comprise a second tube, an optical fiber, and a light source; wherein the second tube may be configured to connect to the light source; wherein the optical fiber may be located within the first tube of the applicator tool and may extend from the applicator tool, through the second tube, and to the light source; and wherein the optical fiber may be configured to emit a light. The light may be configured to sterilize the fluid. The light may be configured to sterilize the skin surface. At least a portion of the applicator tool may be transparent, such that the light is visible to a user when the applicator tool is in use. The skin treatment apparatus may further comprise a ball member and a vacuum tube; wherein the vacuum tube may be connected to the vacuum source; and wherein the ball member may interconnect the applicator tool, the first tube, the second tube, and the vacuum tube. The head of the applicator tool may be configured to rotate via a motor.

Another embodiment may be a skin treatment apparatus, comprising: an applicator tool; a vacuum source; a fluid reservoir; and a first tube; a second tube; an optical fiber; a light source; a ball member; and a vacuum tube; wherein the applicator tool comprises: a tip, a head, and a body; wherein the head is removeably connected to a distal end of the body; wherein the tip is positioned substantially within the head and comprises one or more support members; wherein at least a portion of each of the one or more contact members may be one or more contact surfaces that may be substantially circular and may be fixed on a contacting surface of the tip, such that the contacting surface of the tip is substantially non-planar; wherein the contact surface the tip and the head may be nonabrasive and may be configured to contact a skin surface; wherein the vacuum source provides a vacuum throughout the applicator tool, such that the vacuum is drawn from a distal end of the head and around the tip to a proximal end of the body of the applicator tool to create a suction; wherein the suction is configured to draw a portion of the skin surface into contact with the contact surface of the tip; wherein the tip comprises at least one opening that is in fluid communication with the fluid reservoir via the first tube; wherein the fluid reservoir is configured to store a fluid and to provide the fluid through the at least one opening of the tip of the applicator tool, such that the liquid contacts the skin surface when the head contacts the skin surface; wherein the fluid is configured to pass through the first tube, through the at least one opening of the tip, and drawn outside the tip and within the applicator tool via the vacuum; wherein the second tube is configured to connect to the light source; wherein the optical fiber is located within the first tube of the applicator tool and extends from the applicator tool, through the second tube, and to the light source; wherein the optical fiber is configured to emit a light; wherein the light is configured to sterilize the fluid and the skin surface; wherein at least a portion of the applicator tool is transparent, such that the light is visible to a user when the applicator tool is in use; wherein the vacuum tube is connected to the vacuum source; and wherein the ball member interconnects the applicator tool, the first tube, the second tube, and the vacuum tube.

It is an object to provide a skin treatment apparatus that may utilize an applicator tool with a nonabrasive tip. Preferably, the skin treatment apparatus utilizes a tip with a smooth surface.

It is an object to provide a skin treatment apparatus that may utilize an applicator tip with a rounded surface or flat surface.

It is an object to provide a skin treatment apparatus that may promote stimulation to collagen and growth of new skin cells.

It is an object to provide a skin treatment apparatus that may apply liquid to a skin surface while providing a vacuum mechanism that vacuums or sucks the liquid from the skin surface.

It is an object to provide a skin treatment apparatus that may utilize a motorized rotating replacement head.

It is an object to provide a skin treatment apparatus that may utilize an optical fiber that provides sterilization to the fluid and/or skin surface of individual while providing illumination.

It is an object to provide a skin treatment apparatus that may comprise a transparent or translucent tip, head, shaft and/or body of an applicator tool.

It is an object of the new apparatus to overcome the limitations of the prior art.

Other features and advantages that are inherent in the skin treatment apparatus claimed and disclosed will become apparent to those skilled in the art from the following detailed description and its accompanying drawings.

BRIEF DESCRIPTION OF THE DRAWINGS

The drawings are of illustrative embodiments. They do not illustrate all embodiments. Other embodiments may be used in addition or instead. Details which may be apparent or unnecessary may be omitted to save space or for more effective illustration. Some embodiments may be practiced with additional components or steps and/or without all of the components or steps which are illustrated. When the same numeral appears in different drawings, it refers to the same or like components or steps.

DETAILED DESCRIPTION OF THE ILLUSTRATIVE EMBODIMENTS

In the following detailed description, numerous specific details are set forth in order to provide a thorough understanding of various aspects of one or more embodiments of the disclosure. However, the one or more embodiments may be practiced without some or all of these specific details. In other instances, well-known methods, procedures, and/or components have not been described in detail so as not to unnecessarily obscure aspects of embodiments.

While multiple embodiments are disclosed, other embodiments may become apparent to those skilled in the art from the following detailed description. As will be realized, the following is capable of modifications in various obvious aspects, all without departing from the spirit and scope of the disclosure. Accordingly, the graphs, figures, and the detailed descriptions thereof, are to be regarded as illustrative in nature and not restrictive. Also, the reference or non-reference to a particular embodiment shall not be interpreted to limit the scope of protection.

Before the following is disclosed and described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

In the following description, certain terminology is used to describe certain features of one or more embodiments. For example, the term "abrasive" generally refers to feature of a material or substance used for grinding, polishing, etc. . . . , such as sand, rough particles, emery, pumice, or sandpaper.

Figure 1:
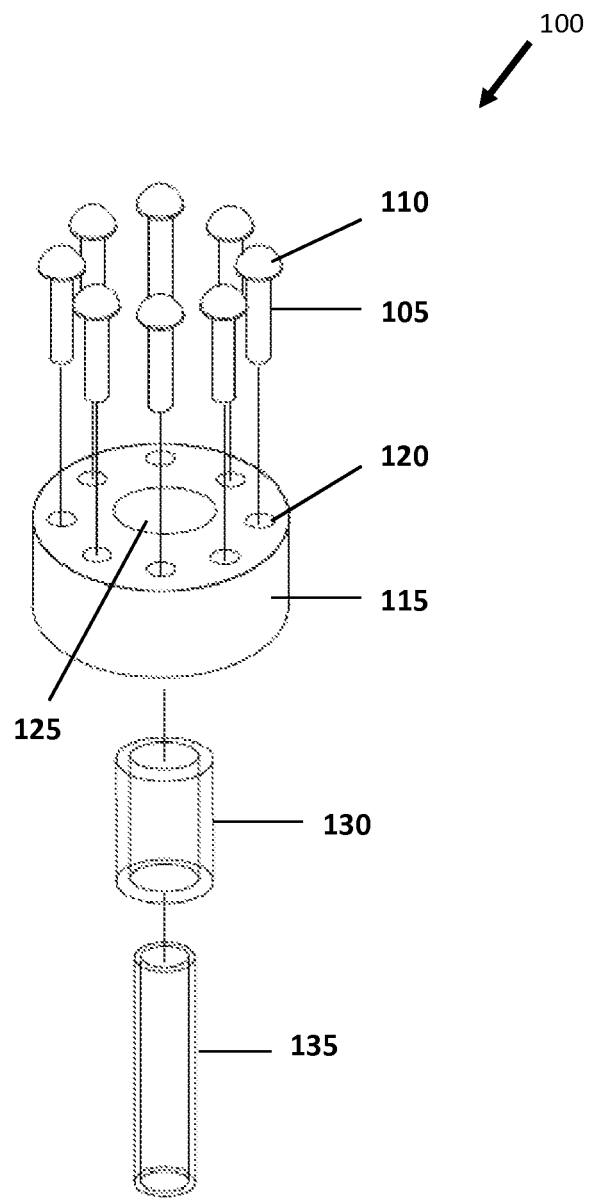
FIG. 1 is an illustration of an exploded view of one embodiment of a tip of an applicator tool of the skin treatment apparatus.
Figure 2:
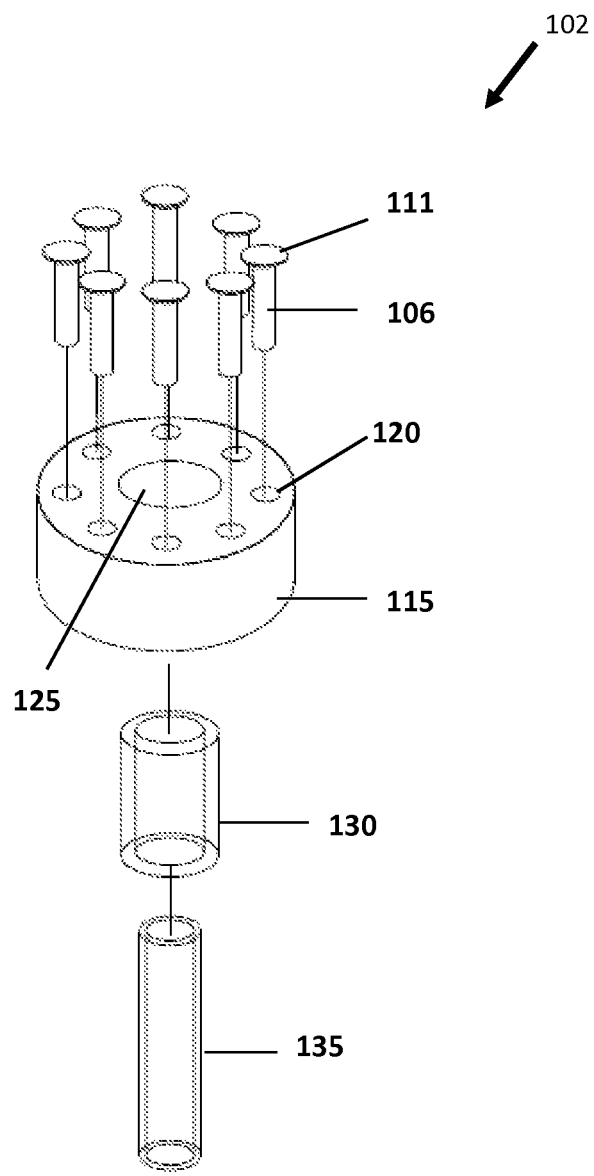
FIG. 2 is an illustration of an exploded view of another embodiment of a tip of an applicator tool of the skin treatment apparatus.

FIG. 1 is an illustration of an exploded view of one embodiment of a tip of an applicator tool of the skin treatment apparatus. As shown in FIG. 1, one embodiment of a tip 100 of an applicator tool 200 (shown in FIGS. 8 to 11) may comprise: one or more contact members 105, a base 115, a fastener 130, and a shaft 135. FIG. 1 shows that the distal end of each of the contact members 105 may comprise a contact surface 110, which, as preferred, is generally smooth and lacks any purposefully abrasive elements. The contact surface 110 is also generally configured to contact a skin surface of a patient. The shape of the contact surface 110 of the contact members 105 may be substantially rounded, as shown in FIG. 1, or may be substantially flat and cylindrical, as shown in FIG. 2. In an alternative embodiment, the shape of the contact surface 110 of the contact members may be spherically shaped and may be held onto the tip 100 via the base 115. Although FIG. 1 shows the shape of the contact surface 110 to be substantially hemispherical, the contact surface 110 may be many different shapes, including, but not limited to, protruding, organic, toroidal, ringed, oval, oblong, round, circular, square, rectangular, conical, cylindrical, elliptical, spherical, polygon, curvilinear, and the like. In another embodiment, the shape of the contact surface 110 may be flat or substantially flat. The proximal end of the contact members 105 may also be configured to engage and fit into holes 120 of the base 115. The fastener 130 preferably mates or engages and fits into the opening 125 of the base 115 and preferably fastens the shaft 135 onto the base 115. Although FIG. 1 shows eight contact members 105, any number of contact members 105 may be attached to the tip such as one or eleven. Additionally, although FIG. 1 shows that a fastener 130 and shaft 135 is used with a tip 100, the tip 100 may be used without a fastener 130 and/or shaft 135, and/or the parts may be integrated as a single part.

FIG. 2 is an illustration of an exploded view of another embodiment of a tip of an applicator tool of the skin treatment apparatus. As shown in FIG. 2, one embodiment of a tip 102 of an applicator tool 200 may comprise: one or more contact members 106, a base 115, a fastener 130, and a shaft 135. FIG. 2 shows that the distal end of each of the contact members 106 may comprise a contact surface 111, which is generally smooth and lacks any purposefully abrasive elements. The contact surface 111 is also generally configured to contact a skin surface of a patient, and the shape of the contact surface 111 of the contact members 106 may be substantially flat, as shown in FIG. 2. Although FIG. 2 shows the shape of the contact surface 111 to be a substantially flat circle or cylindrical shape, the contact surface 111 may be many different shapes, including, but not limited to, protruding, organic, toroidal, ringed, oval, oblong, round, circular, conical, cylindrical, square, rectangular, elliptical, spherical, polygon, curvilinear, and the like. Although FIG. 2 shows eight contact members 106, any number of contact members 106 may be attached to the tip 102 such as one, two, eleven, or over a hundred.

Figure 3:
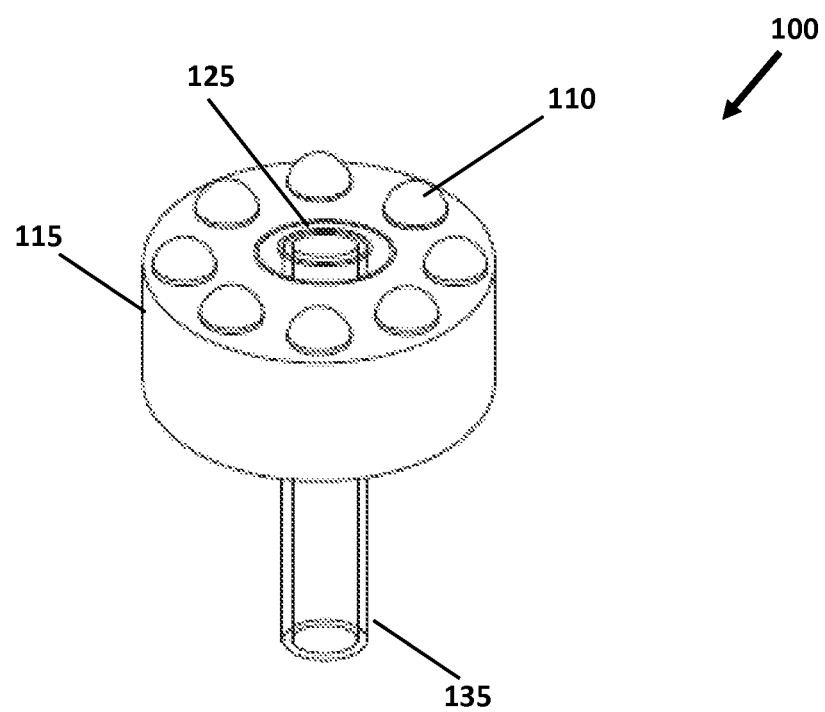
FIG. 3 is an illustration of a top perspective assembled view of one embodiment of a tip of an applicator tool of the skin treatment apparatus.

FIG. 3 is an illustration of a top perspective assembled view of one embodiment of a tip of an applicator tool of the skin treatment apparatus. As shown in FIG. 3, one embodiment of a tip 100 of an applicator tool 200 may comprise: one or more contact surfaces 110 of the contact members 105, a base 115, and a shaft 135. FIG. 3 shows that the contact surface 110 portion of the support member 105 may be exposed for skin contact. Additionally, the tip 100 may comprise an opening 125, which may be configured to allow fluids or liquids to seep through. The contact members 105 are preferably attached to the base of the tip 100, and the contact surfaces 110 may protrude outside the tip 100.

Figure 4:
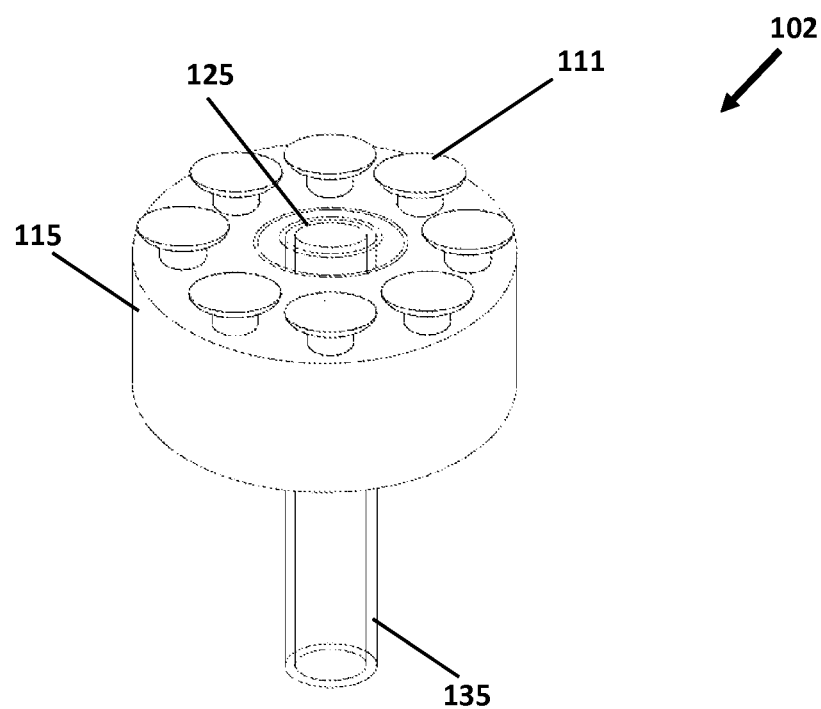
FIG. 4 is an illustration of a top perspective assembled view of another embodiment of a tip of an applicator tool of the skin treatment apparatus.

FIG. 4 is an illustration of a top perspective assembled view of another embodiment of a tip of an applicator tool of the skin treatment apparatus. As shown in FIG. 4, one embodiment of a tip 102 of an applicator tool 200 may comprise: one or more contact surfaces 111 of the contact members 106, a base 115, and a shaft 135. FIG. 4 shows that the contact surface 111 portion of the support member 105 may be protruding from the tip 102 and may be exposed for skin contact. Specifically, although FIG. 4 shows the contact members 106 are preferably attached to the tip 102, the contacting surface of the tip 100 may protrude, such that the contacting surface does not contact the tip 102. Additionally, the tip 102 may comprise an opening 125, which may be configured to allow fluids or liquids to pass or seep through.

Figure 5:
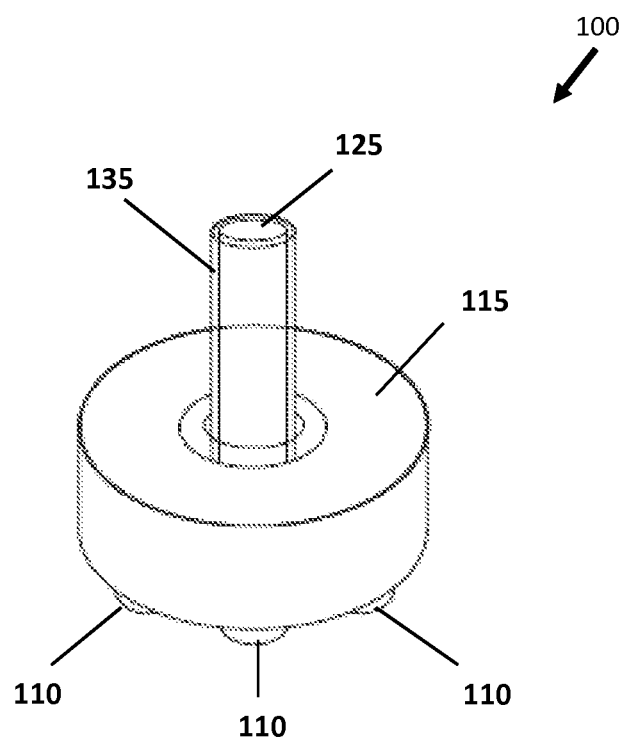
FIG. 5 is an illustration of a bottom perspective assembled view of one embodiment of the tip of an applicator tool of the skin treatment apparatus.

FIG. 5 is an illustration of a bottom perspective assembled view of one embodiment of the tip of applicator tool for the skin treatment apparatus. As shown in FIG. 5, one embodiment of a tip 100 of an applicator tool 200 may comprise: one or more contact surfaces 110 of the contact members 105, a base 115, and a shaft 135. FIG. 5 shows that the opening 125 of the tip 100 may extend through the shaft 135 of the tip 100.

Figure 6:
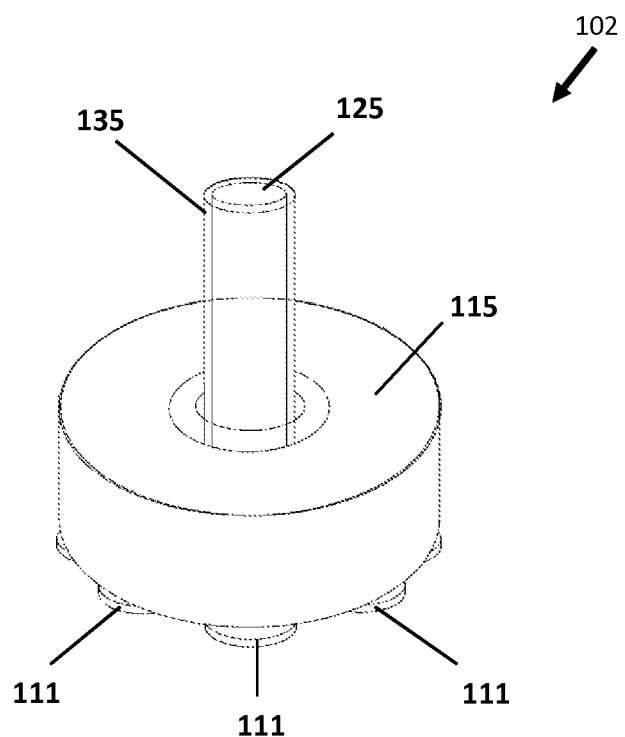
FIG. 6 is an illustration of a bottom perspective assembled view of another embodiment of a tip of an applicator tool of the skin treatment apparatus.

FIG. 6 is an illustration of a bottom perspective assembled view of one embodiment of the tip of applicator tool for the skin treatment apparatus. As shown in FIG. 6, one embodiment of a tip 102 of an applicator tool 200 may comprise: one or more contact surfaces 111 of the contact members 106 (shown in FIG. 2), a base 115, and a shaft 135. FIG. 6 shows that the opening 125 of the tip 100 may extend through the shaft 135 of the tip 102.

Figure 7:
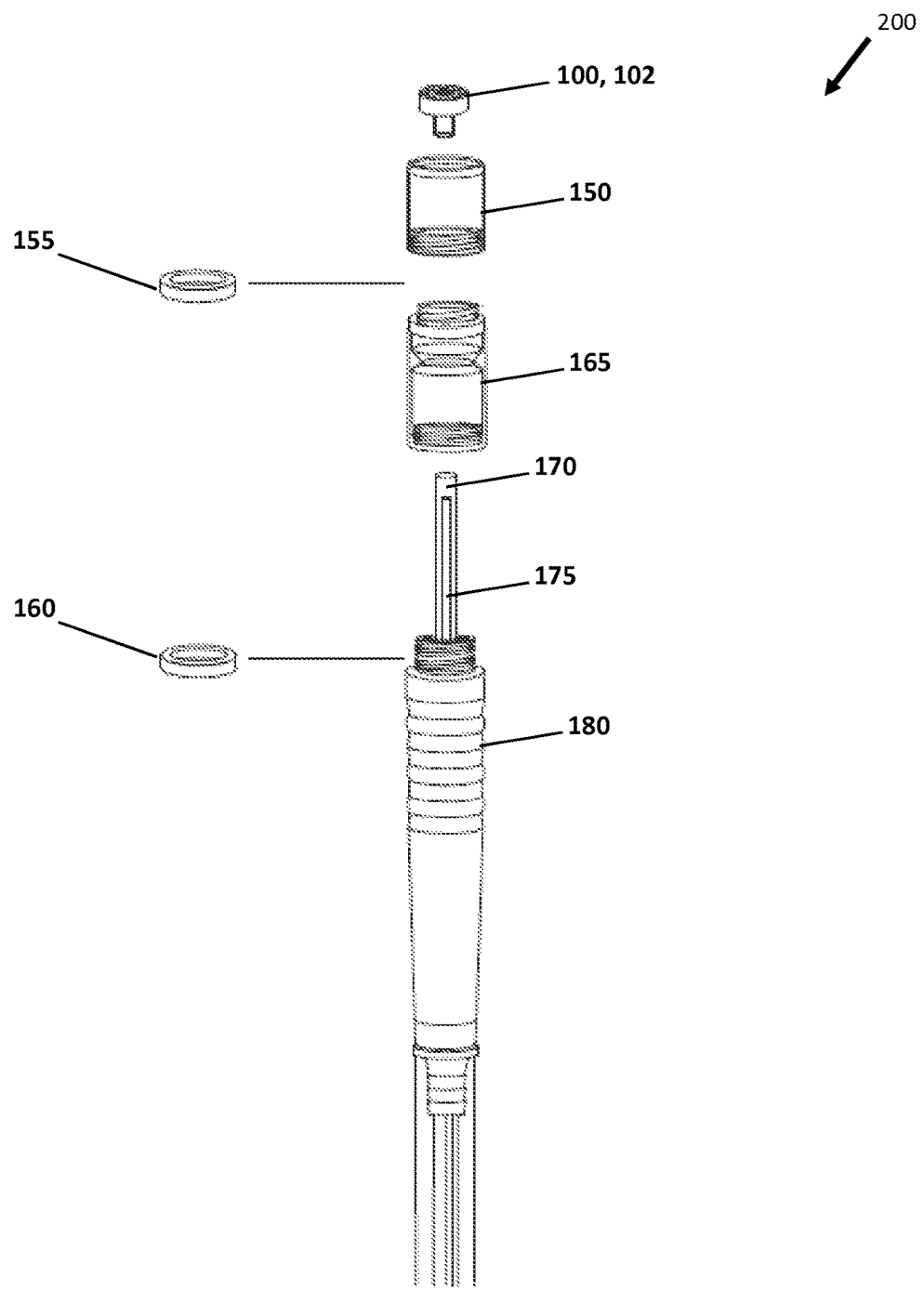
FIG. 7 is an illustration of an exploded view of one embodiment of an applicator tool of the skin treatment apparatus.

FIG. 7 is an illustration of an exploded view of one embodiment of the applicator tool for the skin treatment apparatus. As shown in FIG. 7, one embodiment of the applicator tool 200 may comprise: a tip 100, 102; head 150; O-rings 155, 160; collar 165; first tube 170; optical fiber 175; and body 180. FIG. 7 shows that the optical fiber 175 may be positioned within the first tube 170. The optical fiber 175 is preferably a thin glass fiber through which light may be transmitted throughout the applicator tool 200 and may be configured to sterilize liquid that seeps or passes through the first tube 170. The optical fiber 175 may also be configured to allow the light to sterilize a skin of a patient. In an alternative embodiment, the optical fiber 175 may be positioned outside the first tube 170. The first tube 170 may be positioned within the body 180 of the applicator tool 200 and may extend from the tip 100, 102 and distal end of the applicator tool 200 to the proximal end of the applicator tool 200. FIG. 7 also shows that the collar 165 may engage and connect to the body 180 and that the head 150 may engage and connect to the collar 165. O-rings 155, 160 may also be used to connect in-between the head 150, collar 165, and the body 180. When installed, the tip 100, 102 may be positioned within the head 150 and may connect to the first tube 170 of the applicator tool 200. In another embodiment, the head 150 may rotate in a circular motion via a motor. Although FIG. 7 shows the use of a collar 165 and O-rings 155, 160, the collar 165 and O-rings 155, 160 may be excluded without deviating from the scope of this disclosure.

Figure 8:
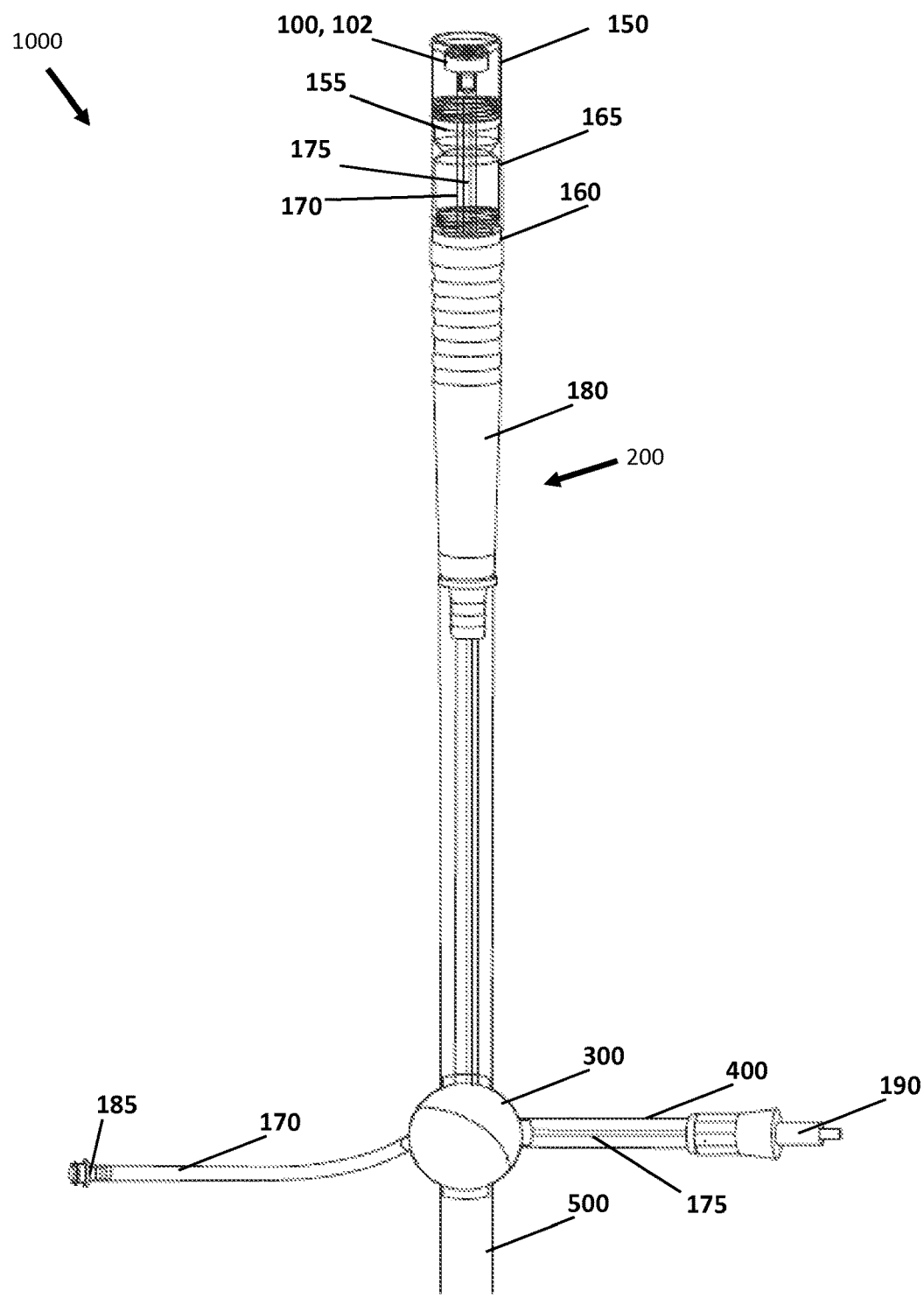
FIG. 8 is an illustration of one embodiment of the skin treatment apparatus.

FIG. 8 is an illustration of one embodiment of the skin treatment apparatus. As shown in FIG. 8, one embodiment of the skin treatment apparatus 1000 may comprise: an applicator tool 200, ball member 300, second tube 400, and vacuum tube 500. One embodiment of the applicator tool 200 may comprise: a tip 100, 102; head 150; O-rings 155, 160; collar 165, first tube 170, optical fiber 175, body 180, and fluid connector 185. An embodiment of the second tube 400 may comprise: the optical fiber 175 and optical connector 190. The head 150 may be connected to the collar 165 with an O-ring 155 in-between, and the collar 165 may be connected to the body 180 with another O-ring 160 in-between. The tip 100, 102 may be connected to the distal end of the first tube 170, which may extend throughout the body 180 of the applicator tool 200 and through the ball member 300. The distal end of the first tube 170 may comprise a fluid connector 185 configured for connecting onto a fluid reservoir device. The second tube 400 may also connect to the ball member 300 and may be used to house the optical fiber 175, which may extend from the tip 100, 102 of the applicator tool 200 to the end of the second tube 400. The optical fiber 175 and second tube 400 may comprise an optical connector 190, which may be configured to connect to a light source for allowing light to be emitted through the second tube 400 and applicator tool 200. In various embodiments, portions of the applicator tool 200 such as the tip 100, 102, head 150, O-rings 155, 160, collar 165, first tube 170, optical fiber 175, and body 180 may be translucent or transparent to allow the fluids and light to be visible to users of the skin treatment apparatus 1000. A vacuum tube 500 may also be connected to the ball member 300 and vacuum source to provide vacuuming or suction for the applicator tool 200.

Figure 9:
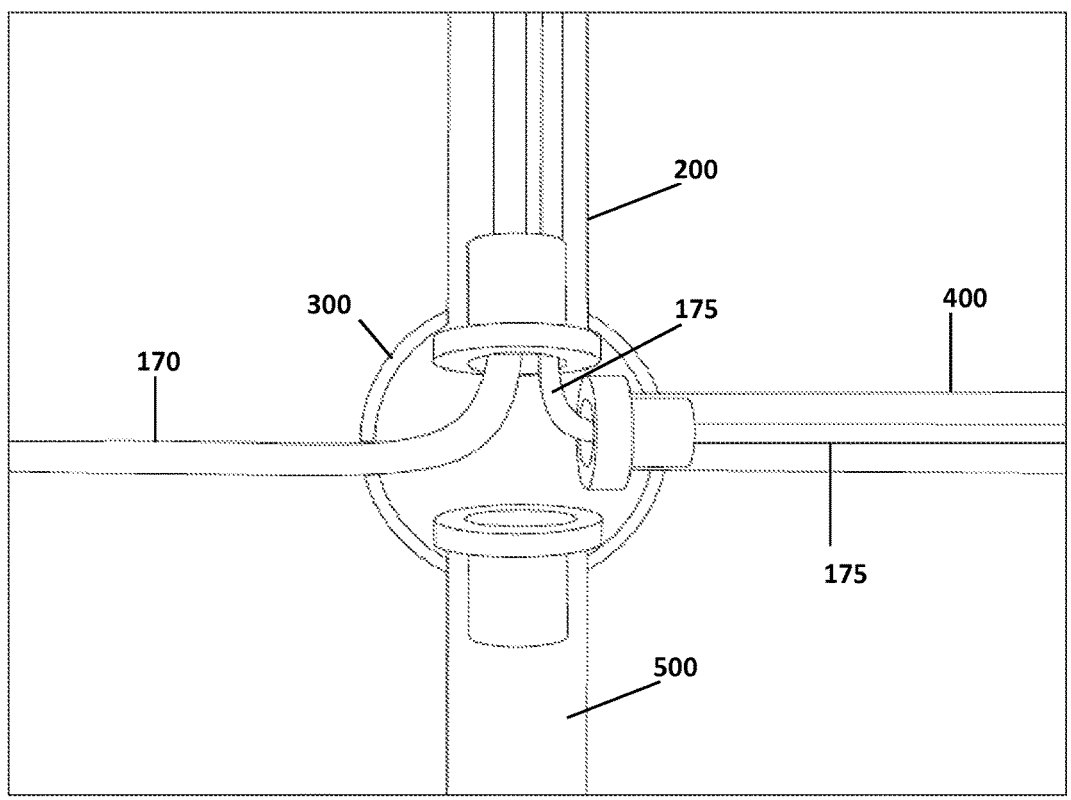
FIG. 9 is an illustration of one embodiment of the ball member of the skin treatment apparatus and shows the inner connections within the ball member.

FIG. 9 is an illustration of one embodiment of the ball member of the skin treatment apparatus and shows the inner connections within the ball member. As shown in FIG. 9, one embodiment of the ball member 300 may connect to the applicator tool 200, first tube 170, second tube 400, and vacuum tube 500. FIG. 9 shows that the proximal end of the applicator tool 200 may be connected to the ball member 300 and that the first tube 170 may extend from the applicator tool 200 and through the ball member 300. The optical fiber 175 may also extend from the applicator tool 200, through the ball member 300, and through the second tube 400. The vacuum tube 300 may connect to the ball member 300.

Figure 10A:
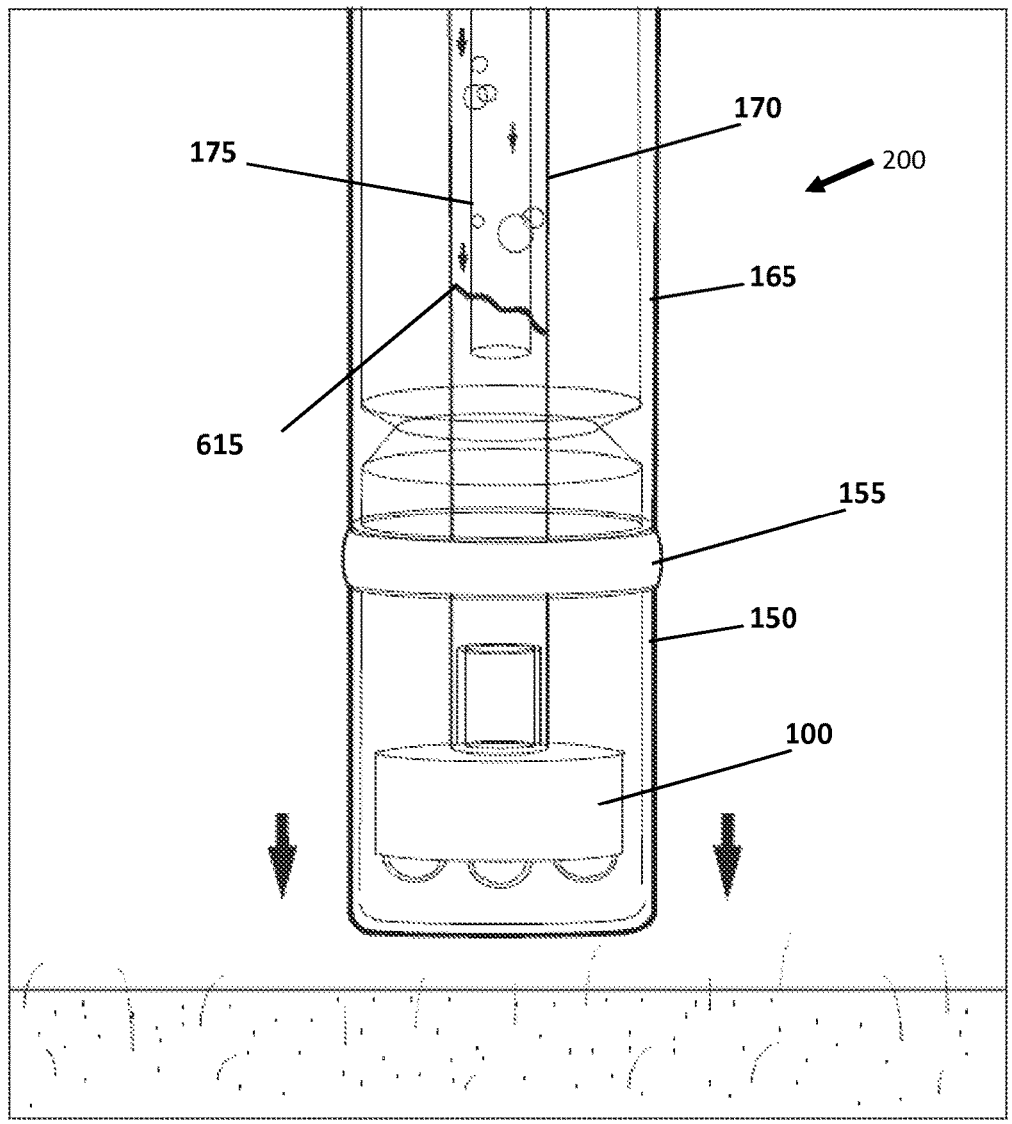
FIGS. 10a and 10b are illustrations of a portion of one embodiment of the applicator tool and show how the applicator tool is applied to the surface of an individual's skin.
Figure 10B:
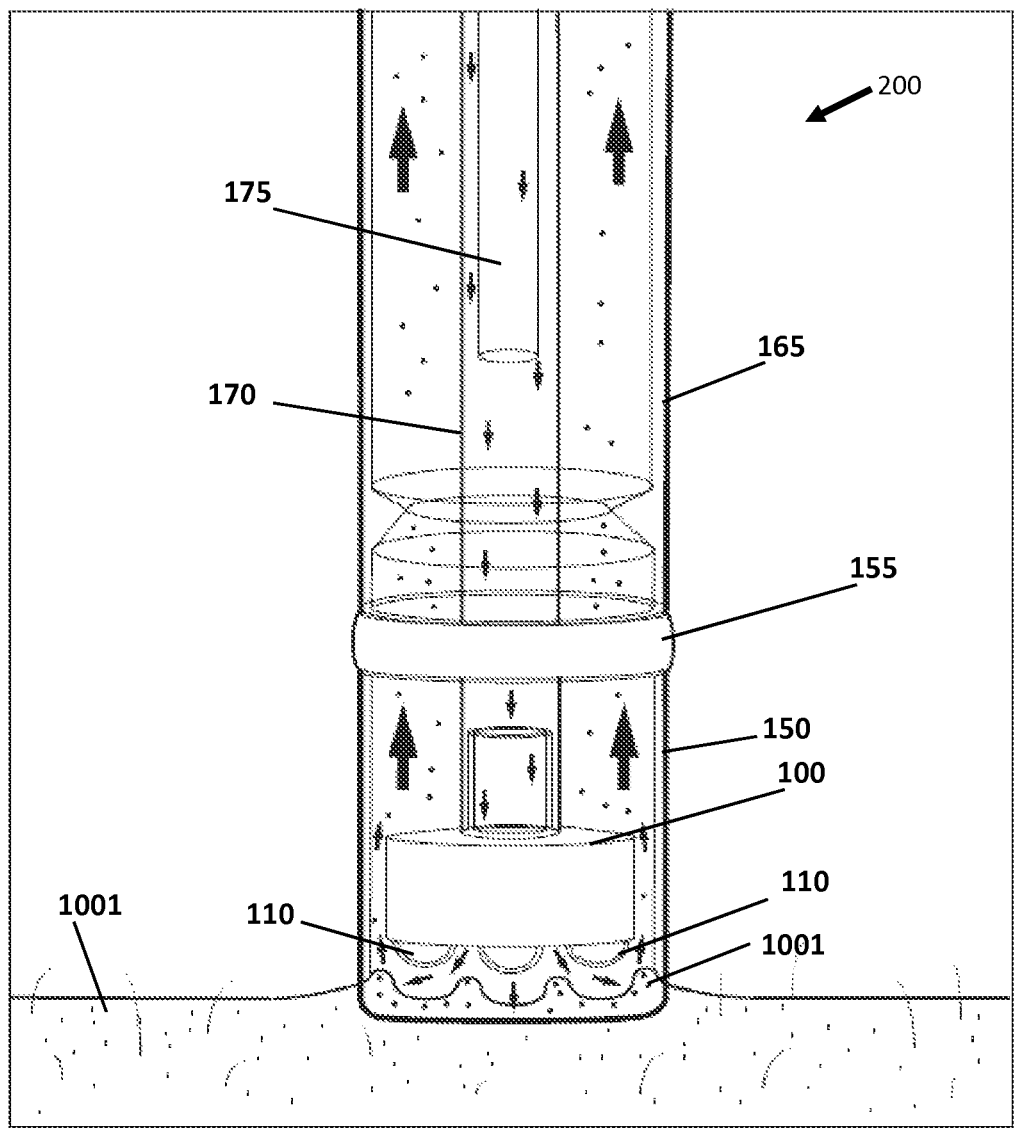

FIGS. 10a and 10b are illustrations of a portion of one embodiment of the applicator tool and show how the applicator tool is applied to a skin surface. As shown in FIGS. 10a and 10b, a portion of one embodiment of an applicator tool 200 may comprise: a tip 100, head 150; O-ring 155, collar 165, first tube 170, and optical fiber 175. FIG. 10a shows that, as the head 150 of the applicator tool 200 is near the skin surface 1001 of an individual, a user may allow fluid to pass through the first tube 170 and around the optical fiber 175. The fluid may then reach the opening of the collar 165 and tip 100. As the head 150 of the applicator tool 200 contacts the skin surface 1001, the fluid may pass through the first tube 170 and exit through the opening of the tip 100. As the applicator tool 200 contacts the skin surface 1001, the fluid may also pass outside the tip 100 and back through the head 150 and collar 165 of the applicator tool 200 via the vacuum or suction, as shown in FIG. 10a. The contact surfaces 110 of the contact members 105 may also contact the skin surface and may massage the skin of the patient. This action may stimulate collagen and skin growth and may allow pores of the skin surface 1001 to open up.

Figure 11A:
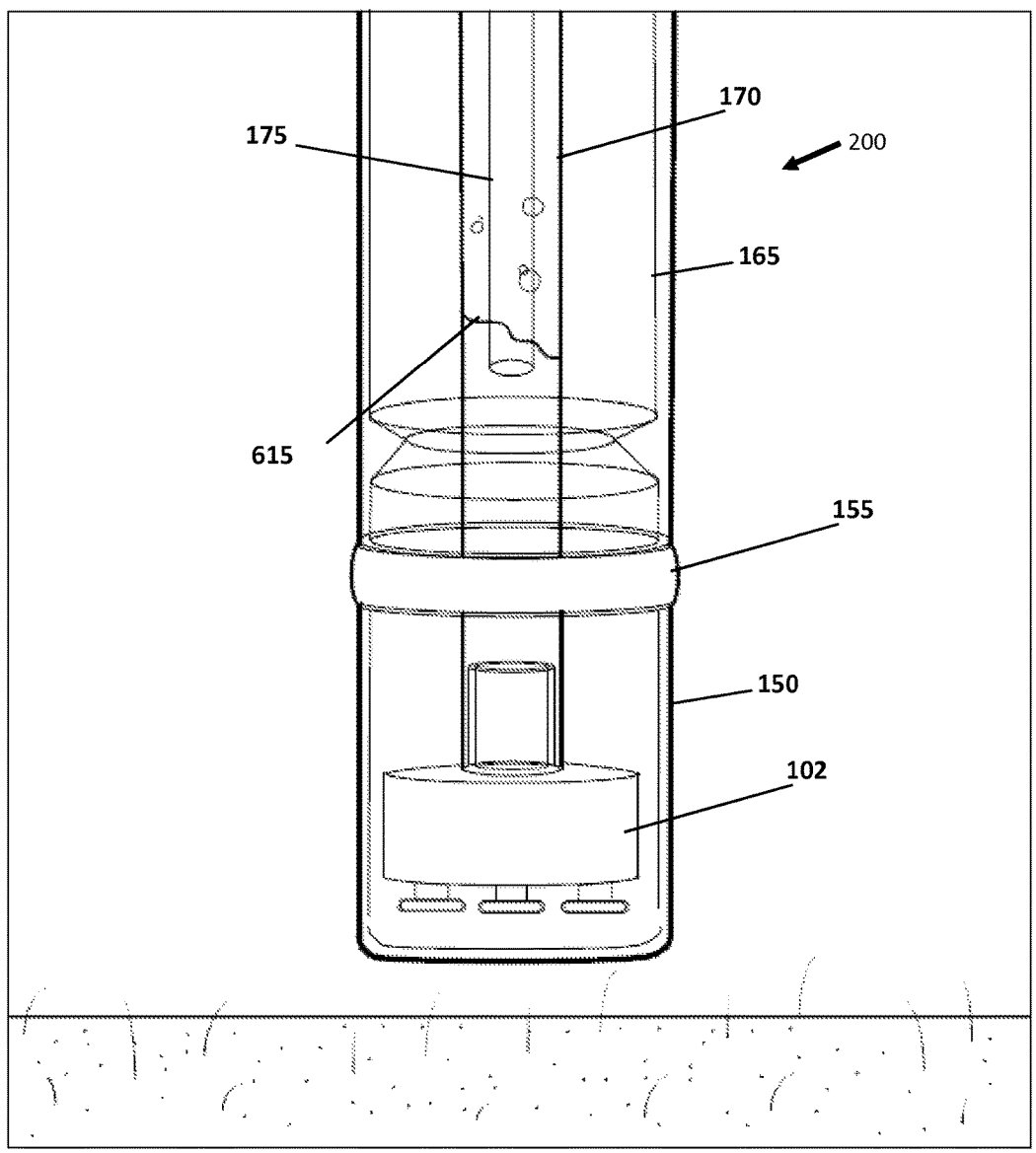
FIGS. 11a and 11b are illustrations of a portion of another embodiment of the applicator tool and show how the applicator tool is applied to the surface of an individual's skin.
Figure 11B:
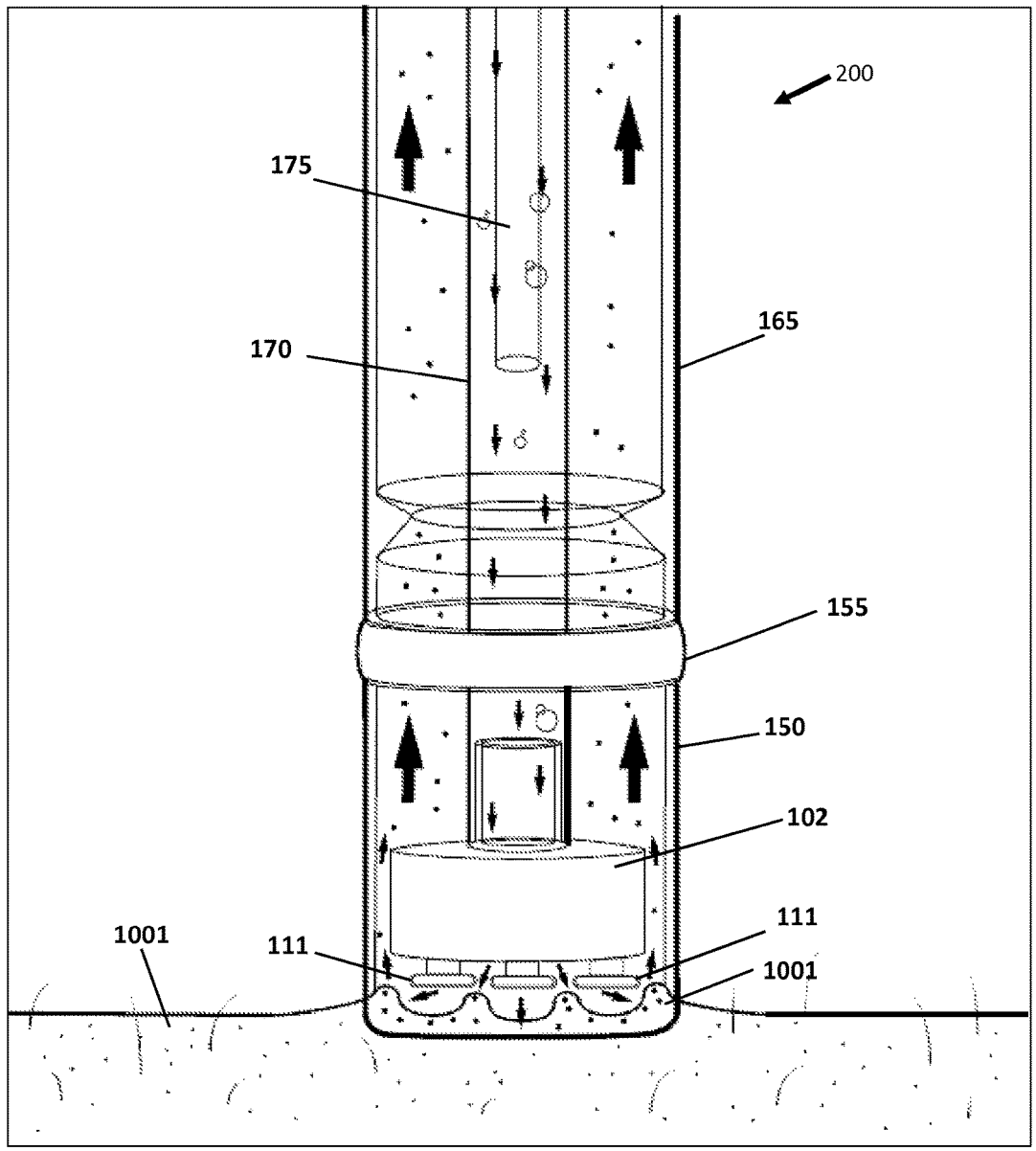

FIGS. 11a and 11b are illustrations of a portion of another embodiment of the applicator tool and show how the applicator tool is applied to a skin surface. Similarly, as shown in FIGS. 11a and 11b, a portion of one embodiment of an applicator tool 200 may comprise: a tip 102, head 150; O-ring 155, collar 165, first tube 170, and optical fiber 175. Like FIG. 10a, FIG. 11a shows that, as the head 150 of the applicator tool 200 is near the skin surface 1001 of an individual, a user may allow fluid to pass through the first tube 170 and around the optical fiber 175. The fluid may then reach the opening of the collar 165 and tip 100. As the head 150 of the applicator tool 200 contacts the skin surface 1001, the fluid may pass through the first tube 170 and exit through the opening of the tip 100. As the applicator tool 200 contacts the skin surface 1001, the fluid may also pass outside the tip 100 and back through the head 150 and collar 165 of the applicator tool 200 via the vacuum or suction, as shown in FIG. 11a. The contact surfaces 110 of the contact members 105 may also contact the skin surface and may massage the skin of the patient. This action may stimulate collagen and skin growth and may allow pores of the skin surface 1001 to open up.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. This disclosure should therefore not be limited by the above described embodiment, method, and examples, but by all embodiments and methods within the scope and spirit of the disclosure as claimed.

The foregoing description of the preferred embodiment has been presented for the purposes of illustration and description. While multiple embodiments are disclosed, still other embodiments will become apparent to those skilled in the art from the above detailed description, which shows and describes illustrative embodiments. As will be realized, the embodiments are capable of modifications in various obvious aspects, all without departing from the spirit and scope. Accordingly, the detailed description is to be regarded as illustrative in nature and not restrictive. Also, although not explicitly recited, one or more embodiments may be practiced in combination or conjunction with one another. Furthermore, the reference or non-reference to a particular embodiment shall not be interpreted to limit the scope. It is intended that the scope not be limited by this detailed description, but by the claims and the equivalents to the claims that are appended hereto.

Except as stated immediately above, nothing which has been stated or illustrated is intended or should be interpreted to cause a dedication of any component, step, feature, object, benefit, advantage, or equivalent to the public, regardless of whether it is or is not recited in the claims.

What is claimed is:

1. A skin treatment apparatus comprising:
   an applicator tool;
   a fluid reservoir;
   a first tube;
   a vacuum source;
   a second tube;
   an optical fiber; and
   a light source;
   wherein said applicator tool comprises: a tip, a head, and a body;
   wherein said head is removeably connected to a distal end of said body;
   wherein said tip is positioned substantially within said head;
   wherein said tip comprises one or more contact members;
   wherein said one or more contact members comprise one or more contact surfaces;
   wherein said one or more contact surfaces of said tip are nonabrasive and are configured to contact a skin surface;
   wherein said vacuum source provides a vacuum throughout said applicator tool, such that said vacuum is drawn from said distal end of said head and around said tip to a proximal end of said body of said applicator tool to create a suction;
   wherein said suction is configured to draw a portion of said skin surface into contact with said one or more contact surfaces of said tip;
   wherein said tip comprises at least one opening that is in fluid communication with said fluid reservoir via said first tube;
   wherein said fluid reservoir is configured to store a fluid and to provide said fluid through said at least one opening of said tip of said applicator tool, such that said fluid contacts said skin surface when said head contacts said skin surface;
   wherein said fluid is configured to pass through said first tube, through said at least one opening of said tip, and drawn outside said tip and within said applicator tool via said vacuum;
   wherein said fluid is a liquid;
   wherein said second tube is configured to connect to said light source;
   wherein said optical fiber is positioned within said first tube of said applicator tool and extends from said applicator tool, through said second tube, and to said light source; and
   wherein said optical fiber is configured to emit a light.

2. The skin treatment apparatus of claim 1, wherein said light is configured to sterilize said fluid.

3. The skin treatment apparatus of claim 1, wherein said light is configured to sterilize said skin surface.

4. The skin treatment apparatus of claim 1, wherein at least a portion of said applicator tool is transparent, such that said light is visible to a user when said applicator tool is in use.

5. The skin treatment apparatus of claim 4, further comprising a ball member and a vacuum tube;
   wherein said vacuum tube is connected to said vacuum source; and
   wherein said ball member interconnects said applicator tool, said first tube, said second tube, and said vacuum tube.

6. The skin treatment apparatus of claim 1, further comprising a ball member and a vacuum tube;
   wherein said vacuum tube is connected to said vacuum source; and
   wherein said ball member interconnects said applicator tool, said first tube, said second tube, and said vacuum tube.

7. The skin treatment apparatus of claim 1, wherein said head of the applicator tool is configured to rotate via a motor.

8. The skin treatment apparatus of claim 1, wherein said one or more contacting surfaces of said tip are substantially flat and cylindrical.

9. The skin treatment apparatus of claim 1, wherein said one or more contact surfaces of said tip are substantially hemispherical.

10. A skin treatment apparatus, comprising:
    an applicator tool;
    a vacuum source;
    a fluid reservoir;
    a first tube;
    a second tube;
    an optical fiber; and
    a light source;
    wherein said applicator tool comprises: a tip, a head, and a body;
    wherein said head is removeably connected to a distal end of said body;
    wherein said tip is positioned substantially within said head and comprises one or more contact members;
    wherein said one or more contact members comprise one or more contact surfaces;
    wherein said one or more contact surfaces of said tip are nonabrasive and are configured to contact a skin surface;
    wherein said vacuum source provides a vacuum throughout said applicator tool, such that said vacuum is drawn from a distal end of said head and around said tip to a proximal end of said body of said applicator tool to create a suction;

wherein said suction is configured to draw a portion of said skin surface into contact with said contact surface of said tip;

wherein said tip comprises at least one opening that is in fluid communication with said fluid reservoir via said first tube;

wherein said fluid reservoir is configured to store a fluid and to provide said fluid through said at least one opening of said tip of said applicator tool, such that said fluid contacts said skin surface when said head contacts said skin surface;

wherein said fluid is configured to pass through said first tube, through said at least one opening of said tip, and drawn outside said tip and within said applicator tool via said vacuum;

wherein said fluid is a liquid.

11. The skin treatment apparatus of claim 10, wherein said second tube is configured to connect to said light source;

wherein said optical fiber is located within said first tube of said applicator tool and extends from said applicator tool, through said second tube, and to said light source; and wherein said optical fiber is configured to emit a light.

12. The skin treatment apparatus of claim 11, wherein said light is configured to sterilize said fluid and skin surface.

13. The skin treatment apparatus of claim 11, wherein at least a portion of said applicator tool is transparent, such that said light is visible to a user when said applicator tool is in use.

14. The skin treatment apparatus of claim 10, wherein said one or more contacting surfaces of said tip are substantially flat and cylindrical.

15. The skin treatment apparatus of claim 10, wherein said one or more contact surfaces of said tip are substantially hemispherical.

16. A skin treatment apparatus, comprising:
- an applicator tool;
- a vacuum source;
- a fluid reservoir;
- a first tube;
- a second tube;
- an optical fiber;
- a light source;
- a ball member; and
- a vacuum tube;

wherein said applicator tool comprises: a tip, a head, and a body;

wherein said head is removeably connected to a distal end of said body;

wherein said tip is positioned substantially within said head and comprises one or more contact members;

wherein said one or more contact members comprise one or more contact surfaces;

wherein said one or more contact surfaces of said tip are nonabrasive and are configured to contact a skin surface;

wherein said one or more contacting surfaces of said tip are substantially flat and cylindrical;

wherein said vacuum source provides a vacuum throughout said applicator tool, such that said vacuum is drawn from a distal end of said head and around said tip to a proximal end of said body of said applicator tool to create a suction;

wherein said suction is configured to draw a portion of said skin surface into contact with said contact surface of said tip;

wherein said tip comprises at least one opening that is in fluid communication with said fluid reservoir via said first tube;

wherein said fluid reservoir is configured to store a fluid and to provide said fluid through said at least one opening of said tip of said applicator tool, such that said fluid contacts said skin surface when said head contacts said skin surface;

wherein said fluid is configured to pass through said first tube, through said at least one opening of said tip, and drawn outside said tip and within said applicator tool via said vacuum;

wherein said second tube is configured to connect to said light source;

wherein said optical fiber is located within said first tube of said applicator tool and extends from said applicator tool, through said second tube, and to said light source;

wherein said optical fiber is configured to emit a light;

wherein said light is configured to sterilize said fluid and said skin surface;

wherein at least a portion of said applicator tool is transparent, such that said light is visible to a user when said applicator tool is in use;

wherein said vacuum tube is connected to said vacuum source;

wherein said ball member interconnects said applicator tool, said first tube, said second tube, and said vacuum tube; and wherein said fluid is a liquid.

\* \* \* \* \*